(12) United States Patent
Ryan

(10) Patent No.: US 11,857,753 B2
(45) Date of Patent: Jan. 2, 2024

(54) DISINFECTING SYRINGE TIP

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 401 days.

(21) Appl. No.: 17/120,529

(22) Filed: Dec. 14, 2020

(65) Prior Publication Data

US 2021/0187266 A1 Jun. 24, 2021

Related U.S. Application Data

(60) Provisional application No. 62/952,830, filed on Dec. 23, 2019.

(51) Int. Cl.
*A61M 39/16* (2006.01)
*A61M 5/30* (2006.01)

(52) U.S. Cl.
CPC .......... *A61M 39/16* (2013.01); *A61M 5/3007* (2013.01); *A61M 2205/0205* (2013.01); *A61M 2205/0222* (2013.01)

(58) Field of Classification Search
CPC ................ A61M 39/16; A61M 5/3007; A61M 2205/0205; A61M 39/162
See application file for complete search history.

(56) References Cited

U.S. PATENT DOCUMENTS 4,597,758 A 7/1986 Aalto et al.
4,642,102 A 2/1987 Ohmori
(Continued)

FOREIGN PATENT DOCUMENTS

CN 101631585 A 1/2010
CN 103025374 A 4/2013
(Continued)

OTHER PUBLICATIONS

Final Office Action in U.S. Appl. No. 16/253,683, dated Dec. 23, 2020, 9 pages.
(Continued)

*Primary Examiner* — Bradley J Osinski
(74) *Attorney, Agent, or Firm* — Servilla Whitney LLC

(57) ABSTRACT

A disinfection tip is described for disinfecting a threaded connector of a syringe. The disinfection tip includes a cylindrical outer housing, a substantially cylindrical inner housing extending from a distal wall of the outer housing, a distal chamber defined by the outer sidewall of the inner housing, the inner wall of the outer housing and the distal wall of the outer housing, the distal chamber being in fluid communication with the cavity, the distal chamber retaining a disinfectant or antimicrobial agent when the disinfection tip is disposed within an outer wall of the luer connector of the syringe and, at least one jet orifice radially disposed on the inner rim in fluid communication with the distal chamber allowing for fluid to pass from the distal chamber through the jet orifice directing the disinfectant or antimicrobial agent towards a center of the outer housing when the disinfection tip is further inserted into the luer connector of the syringe, the insertion of the disinfection tip causing the volume of the distal chamber to reduce and expel disinfectant or antimicrobial agent through the at least one jet orifice.n

20 Claims, 9 Drawing Sheets

(56) References Cited

U.S. PATENT DOCUMENTS

| | | | |
|---|---|---|---|
| 4,711,363 | A | 12/1987 | Marino |
| 4,738,376 | A | 4/1988 | Markus |
| 4,906,231 | A | 3/1990 | Young |
| 5,084,017 | A | 1/1992 | Maffetone |
| 5,496,288 | A | 3/1996 | Sweeny |
| 5,984,123 | A | 11/1999 | Mogami et al. |
| 6,565,529 | B1 | 5/2003 | Kimber et al. |
| 8,012,131 | B2 | 9/2011 | Moser et al. |
| 8,172,825 | B2 * | 5/2012 | Solomon ............. A61M 39/162 604/905 |
| 10,871,246 | B2 | 12/2020 | Marici et al. |
| 2003/0093009 | A1 | 5/2003 | Newby et al. |
| 2008/0171995 | A1 | 7/2008 | Mtullo et al. |
| 2009/0205151 | A1 * | 8/2009 | Fisher ................. B08B 9/021 15/104.04 |
| 2011/0046603 | A1 | 2/2011 | Felsovalyi et al. |
| 2012/0123386 | A1 | 5/2012 | Tsals |
| 2014/0150832 | A1 | 6/2014 | Rogers et al. |
| 2018/0085568 | A1 * | 3/2018 | Drmanovic ......... A61M 5/3134 |
| 2018/0237190 | A1 | 8/2018 | Iwasaki |
| 2019/0232039 | A1 | 8/2019 | Erekovcanski et al. |
| 2021/0187267 | A1 | 6/2021 | Jiang |

FOREIGN PATENT DOCUMENTS

| | | |
|---|---|---|
| CN | 206315311 U | 7/2017 |
| DE | 202005004079 U1 | 7/2006 |
| JP | 2008532701 A | 8/2008 |
| WO | 2014159346 A1 | 10/2014 |
| WO | 2015121602 A1 | 8/2015 |
| WO | 2017087400 A1 | 5/2017 |
| WO | 2020112767 A1 | 6/2020 |

OTHER PUBLICATIONS

"Non-Final Office Action in U.S. Appl. No. 16/378,015, dated Mar. 30, 2021, 10 pages".

"PCT International Search Report and Written Opinion in PCT/US2020/057611 dated Feb. 5, 2021, 11 pages".

"PCT International Search Report and Written Opinion in PCT/US2020/065229 dated Mar. 29, 2021, 11 pages".

PCT International Search Report and Written Opinion in PCT/US2020/065228 dated Mar. 29, 2021, 12 pages.

* cited by examiner

DISINFECTING SYRINGE TIP

CROSS-REFERENCE TO RELATED APPLICATIONS

This application claims priority under 35 U.S.C. § 119(e) to U.S. Provisional Application No. 62/952,830, filed Dec. 23, 2019, the disclosures of which are incorporated herein by reference in their entirety.

TECHNICAL FIELD

The present disclosure relates to disinfection devices for disinfecting corresponding medical connectors. The present disclosure generally relates to a device for automatically disinfecting and sterilizing access ports of medical connectors when attaching the access port to a threaded or interlocking fitting. Generally, exemplary embodiments of the present disclosure relate to the fields of threaded or interlocking fittings, including medical disinfection means, and in particular disinfection tips for uses with threaded fluid connectors. Exemplary embodiments of the present disclosure relate to disinfection tips for disinfecting male threaded luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hub, port, or valve upon connection to the VAD to deliver the fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures.

In developed markets, when utilizing an IV catheter, a needleless connector will typically be used to close off the system and then subsequently accessed to administer medication or other necessary fluids via the catheter to the patient. Infusion Nurses Society ("INS") Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

The need to protect medical connectors to reduce CLABSI and PLABSI has been rising. IV gravity sets and threaded connections on syringes are subject to contamination when not protected properly. Currently when IV connectors are disconnected from central lines or peripheral lines to temporarily discontinue infusion, nurses often loop the male connector to a Y-site needle-free connector or wrap the male connector in a piece of Isopropyl Alcohol ("IPA")/alcohol impregnated wipe or cloth. However such protection is very weak and does not protect the luer from touch contamination properly.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

VAD standards and practices commonly include disinfecting both the threaded male connector and the IV catheter connection. The additional steps increase the likelihood of contamination while also increasing the likelihood of non-compliance with disinfection procedures. Disinfectants typically have a threshold limit for systemic exposure for infusion into blood stream due to biotoxicity of the disinfectants at high dosage. Thus, there is a need for a disinfection device capable of disinfecting both the lumen of open luers and the corresponding IV connector. There is a need for a syringe tip which is able to disinfect an IV needleless connector during syringe use therefore saving the clinician time and reducing work steps. There is a need for a mechanism to reducing steps in preventing contamination of VAD devices.

SUMMARY

The present disclosure relates to a disinfection tip comprising a substantially cylindrical outer housing, the outer housing having an outer wall, a distal wall, and an open proximal surface, a cavity defined by an aperture extending from the open proximal surface to the distal wall, the distal wall having an opening defining an inner rim and an inner wall, a substantially cylindrical inner housing extending from the inner rim in a proximal direction at least partially a length of the outer housing, the inner housing having an inner proximal surface, an inner sidewall and an outer sidewall, the inner sidewall forms a liquid-tight seal with an abutting tapered tip of a luer connector when the disinfection tip is disposed at least partially within the luer connector, a distal chamber defined by the outer sidewall of the inner housing, the inner wall and the distal wall of the outer housing, the distal chamber being in fluid communication with the cavity, the distal chamber retaining a disinfectant when the disinfection tip is at least partially disposed within an outer wall of the luer connector of the luer connector and at least one jet orifice radially disposed on the inner rim, the jet orifice having an inlet, an outlet and a channel extending from the inlet to the outlet.

In one or more embodiments, a cylindrical body of an IV connector is advanced against the distal wall of the outer housing of the disinfection tip, the IV connector further inserting the disinfection tip into the luer connector, whereby a tapered tip of the luer connector engages with a lumen of the cylindrical body of the IV connector, the advancement causing the disinfectant to ejected from the at least one orifice, and the disinfectant further disinfects the lumen of the IV connector.

In one or more embodiments, an outer wall of the luer connector includes a plurality of threads for engaging at least one thread of the disinfection tip and at least one of a plurality of threads of an IV connector, the at least one thread disposed on a cylindrical body of the IV connector.

In one or more embodiments, threading the IV connector onto the luer connector transfers an axial force and torque to the disinfection tip, the threading of the IV connector causing the advancement of the disinfection tip.

In one or more embodiments, the distal wall of the disinfection tip is smooth in order to limit torque coupling during unthreading of the IV connector from the luer connector.

In one or more embodiments, the distal wall of the disinfection has a rough or textured surface to promote torque coupling.

In one or more embodiments, the distal wall of the disinfection has at least one radial spline configured to engage with the IV connector.

In one or more embodiments, the distal wall of the disinfection has at least one gear tooth configured to engage with a corresponding tooth of the IV connector, the at least one gear tooth configured to promote torque coupling.

In one or more embodiments, the distal wall of the disinfection includes a plurality of radial peaks, in which an incline of the peak is at a right angle with the distal wall while a decline of the peak is at an acute angle with the distal wall, wherein the incline allows for a feature of the IV connector to advance the disinfection tip in the direction of the incline, while the decline prohibits opposite direction of advancement, the direction of advancement being the same direction in which the IV connector is threaded onto the luer connector of the luer connector.

In one or more embodiments, the inlet of the at least one jet orifice is in fluid communication with the distal chamber allowing for the disinfectant or antimicrobial agent to pass from the distal chamber through the channel to the outlet.

In one or more embodiments, the outlet of the at least one jet orifice is disposed on the rim.

In one or more embodiments, the outlet of the at least one jet orifice is positioned to direct the disinfectant or antimicrobial agent from the distal chamber in a distal direction towards a center of the outer housing.

In one or more embodiments, insertion of the disinfection tip allows a volume of the distal chamber to reduce and expel disinfectant or antimicrobial agent through the at least one jet orifice.

In one or more embodiments, the disinfectant disinfects the cylindrical body of the IV connector.

In one or more embodiments, the disinfectant evacuates though a tolerance gap between a plurality of threads of the IV connector and a plurality of threads of the syringe.

In one or more embodiments, at least one thread of the IV connector fully engages at least one of a plurality of threads of the IV connector.

In one or more embodiments, the disinfection tip may be in a fully threaded position while still permitting the IV connector to sufficiently thread into the luer connector.

In one or more embodiments, the disinfection tip may be in a fully threaded position while still permitting the IV connector to sufficiently thread into the luer connector in compliance with ISO594-2 standards.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Figure 1:
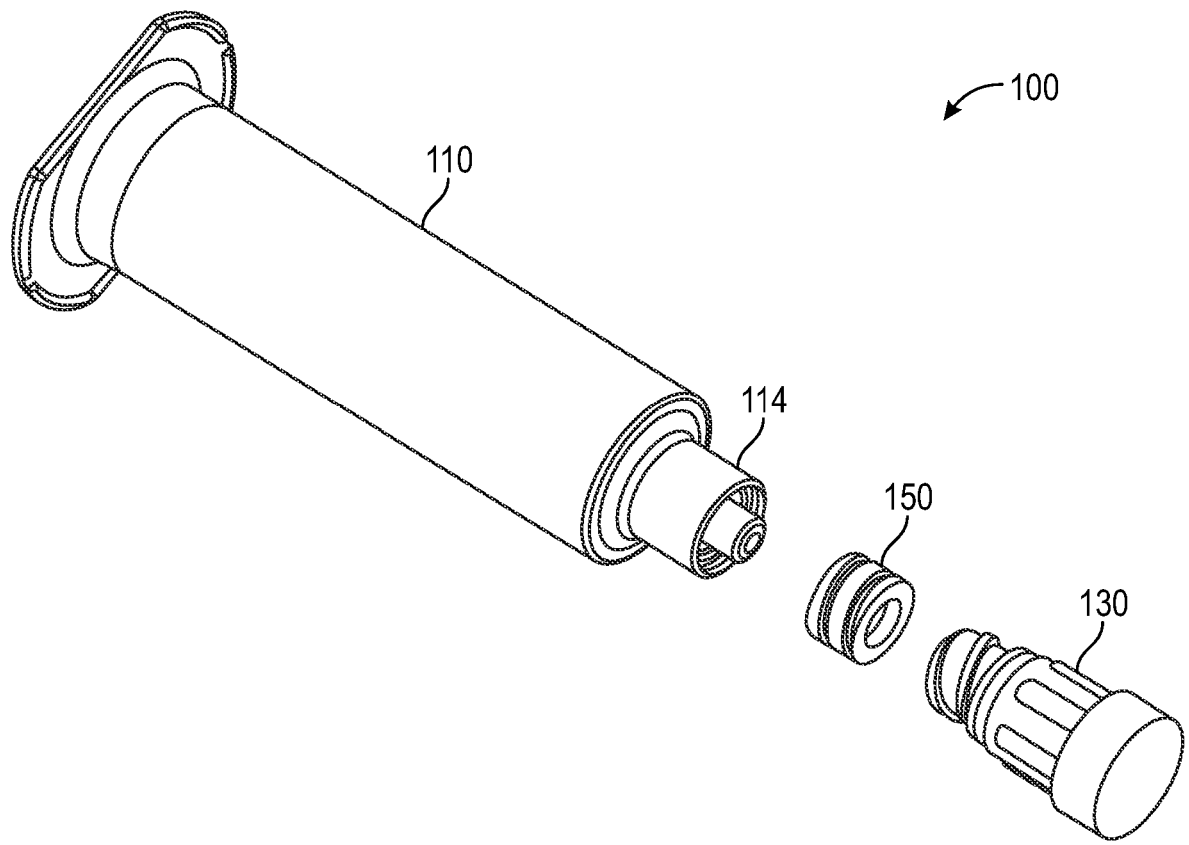
FIG. 1 illustrates an exploded perspective view of a disinfection system 100 in accordance with an exemplary first embodiment of the disclosure.

Embodiments of the present disclosure pertain to a disinfection cap for connection to and disinfection of a medical connector, including threaded connectors. In one or more embodiments, the connectors are male luer connectors or female luer connectors. The disclosure aims to provide a mechanism capable of disinfecting both the lumen of open luers and the corresponding IV connector while minimizing additional steps in medical administration. It is contemplated that the disinfection cap disclosed herein can be utilized with male or female threaded connectors. The disclosure aims to provide a mechanism to disinfect an IV needleless connector during syringe use, therefore saving the clinician time and reducing work steps. The disclosure aims to reducing the number of steps required in preventing contamination of VAD devices.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and male interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the male end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As used herein, the term "syringe" refers to a simple pump-like device consisting of a plunger rod that fits tightly in a barrel or tube. The plunger rod can be pulled or advanced along inside the barrel, allowing the syringe to take in and expel a liquid or gas through an opening at the open end of the barrel.

As used herein, the term "medical device" refers to common medical devices having threaded or interlocking connections, the connections having corresponding mating elements. By way of example but not limitation, a syringe has a male threaded connection which releasably interlocks with a secondary medical device such as a male luer connection of a catheter, an IV line and the like. The threaded connection includes a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness. Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Referring to FIG. 1, the present disclosure includes a disinfection system 100 comprising a syringe 110 having a threaded connector such as a luer connector 114, a disinfection tip 150 which is disposed at least partially within the luer connector 114 of the syringe 110 and an IV connector 130 which advances the disinfection tip 150 further into the luer connector 114 of the syringe as the IV connector 130 is threaded into the threaded connection of the syringe 110; the disinfection tip 150 being advanced in a proximal direction. In one or more embodiments, the disinfection tip 150 is fully disposed within the luer connector 114. In one or more embodiments, a disinfectant or antimicrobial agent 102 (hereinafter "disinfectant 102," not shown) is retained in a volume between the luer connector 114 and the disinfection tip 150, defining a disinfectant chamber 124 when the disinfection tip 150 is at least partially disposed within the luer connector 114. In one or more embodiments, the disinfection tip 150 is fully disposed within the luer connector 114. In one or more embodiments, the disinfectant 102 is a fluid or gel.

In an exemplary implementation of the embodiments of present disclosure, the disinfection tip 150 includes integrated threads or tabs, and other features in any and all combinations allowing it to interface with a threaded fitting of a medical device. In preferred embodiments, the disinfection tip 150 interfaces with a male Luer fitting. Exemplary configurations for couplers, fittings, ports and adapters may include commercially available luer locks, luer slip ports, locking ports, threaded connections, interlocking connection or generally other common medical device fitting known in the art.

Figure 2:
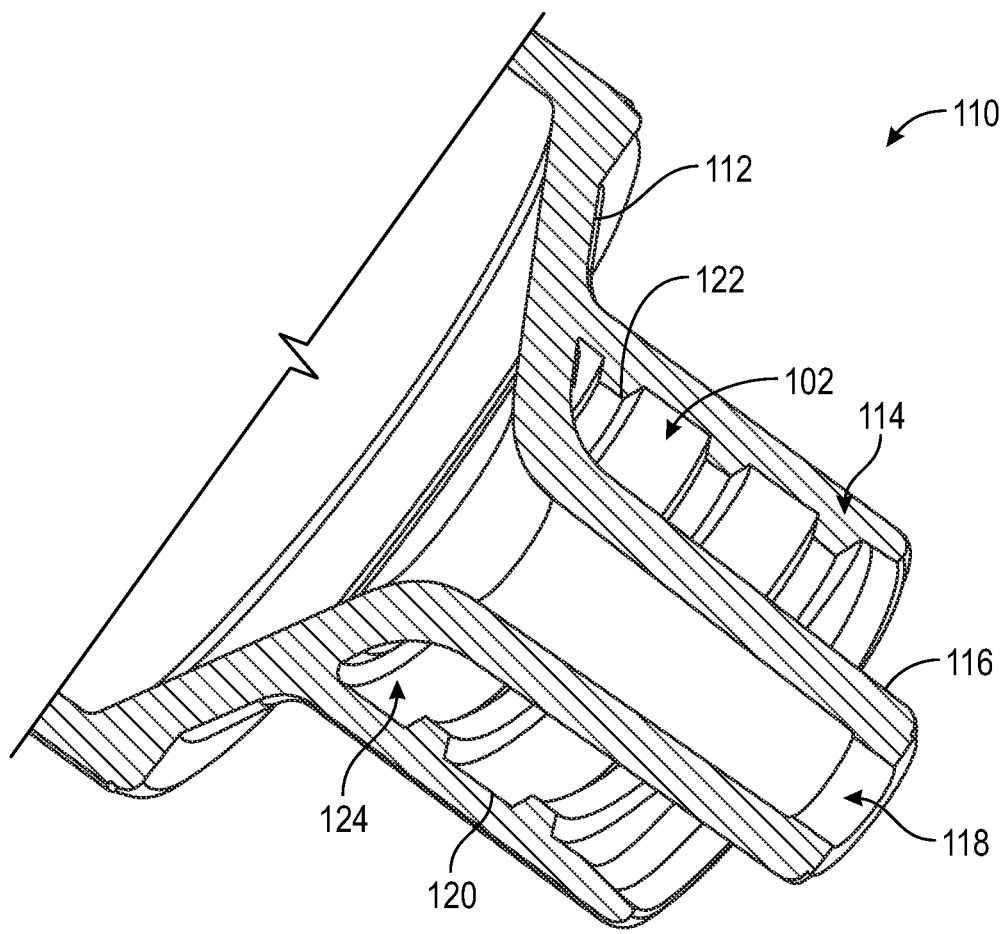
FIG. 2 illustrates a cross-sectional view of a syringe tip in accordance with an exemplary first embodiment of the disclosure.

Referring to FIG. 2, the syringe 110 includes a conical base 112 disposed on the distal end of the barrel of the syringe 110. A luer connector 114 is distally disposed on the conical base 112, the luer connector including a tapered tip 116 and an integrally formed outer collar 120. The tapered tip 116 extends from the conical base 112 of the syringe and has a substantially conical shape. The outer collar 120 of the syringe 110 includes a plurality of threads 122 for engaging a plurality of threads 138 of the IV connector 130. A lumen 118 is disposed within the tapered tip 116, extending through the tapered tip 116 and the conical base 112, the lumen opening being in fluid communication from the barrel of the syringe 110 to the IV connector 130 which connects to the luer connector 114 by a preferably threaded connection. Finally, a cavity is defined between the tapered tip 116 and the outer collar 120, the cavity defining a volume in which disinfectant 102 is retained.

In further embodiments, the syringe includes a flat base. In further embodiments, the integrally formed outer collar 120 lacks threads, in which secondary attachment devices are retained by a press-fit, interference fit or an interlocking push and twist-lock fit. In one or more embodiments in which the outer collar 120 lacks threads, the luer connector 114 is connected to the IV connector 130 by an interference fit between the lumen 134 of the IV connector 130 and the luer connector 114 of the syringe 110. In one or more embodiments include any device having a luer or threaded connector, by way of example, a sample collection container such as a VACUTAINER®, provided by Becton Dickinson and Company. The sample collection container including a threaded or slip fit luer connector.

Figure 3:
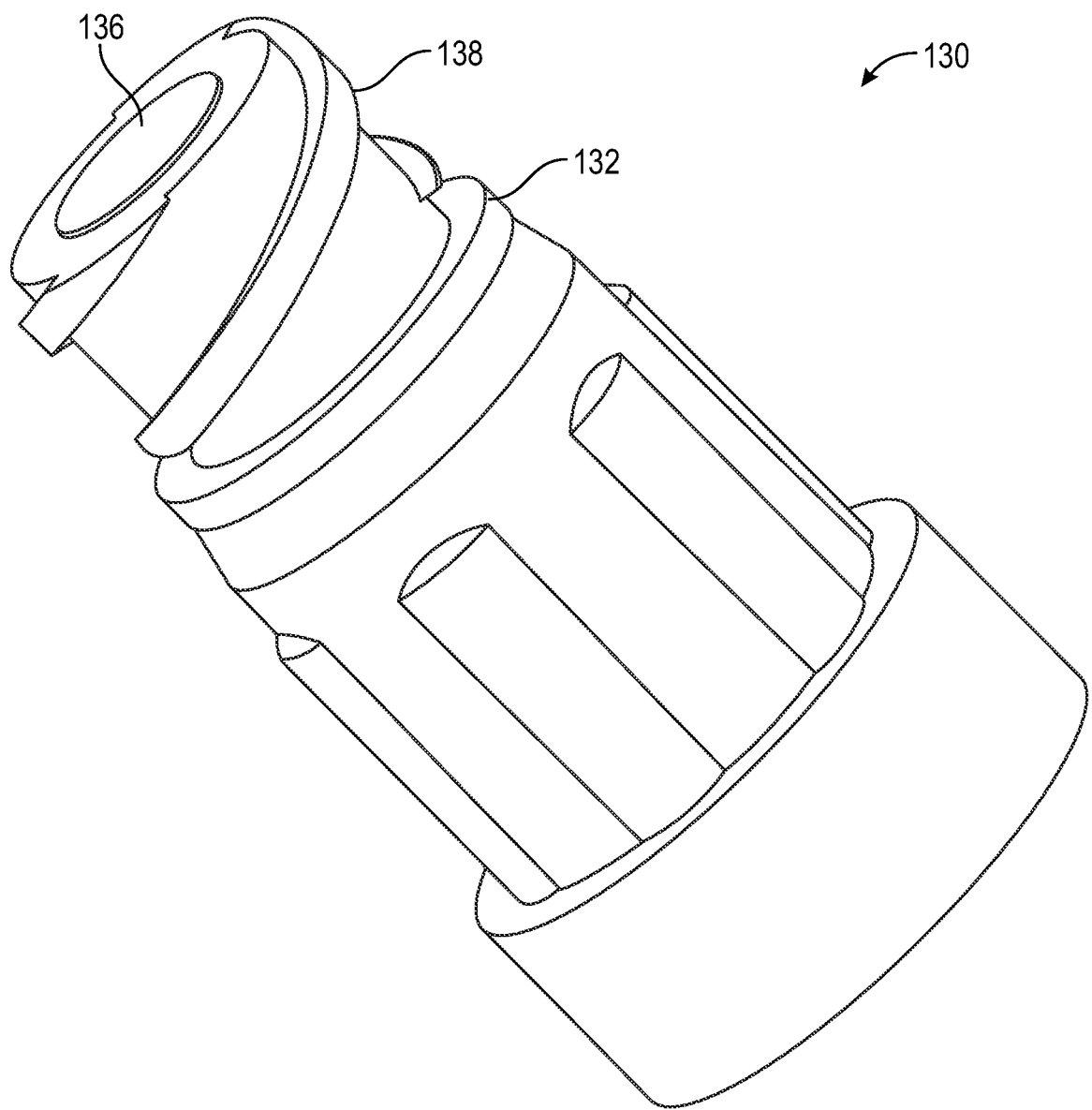
FIG. 3 illustrates a perspective view of an intravenous connector according to an exemplary first embodiment of the disclosure.
Figure 4:
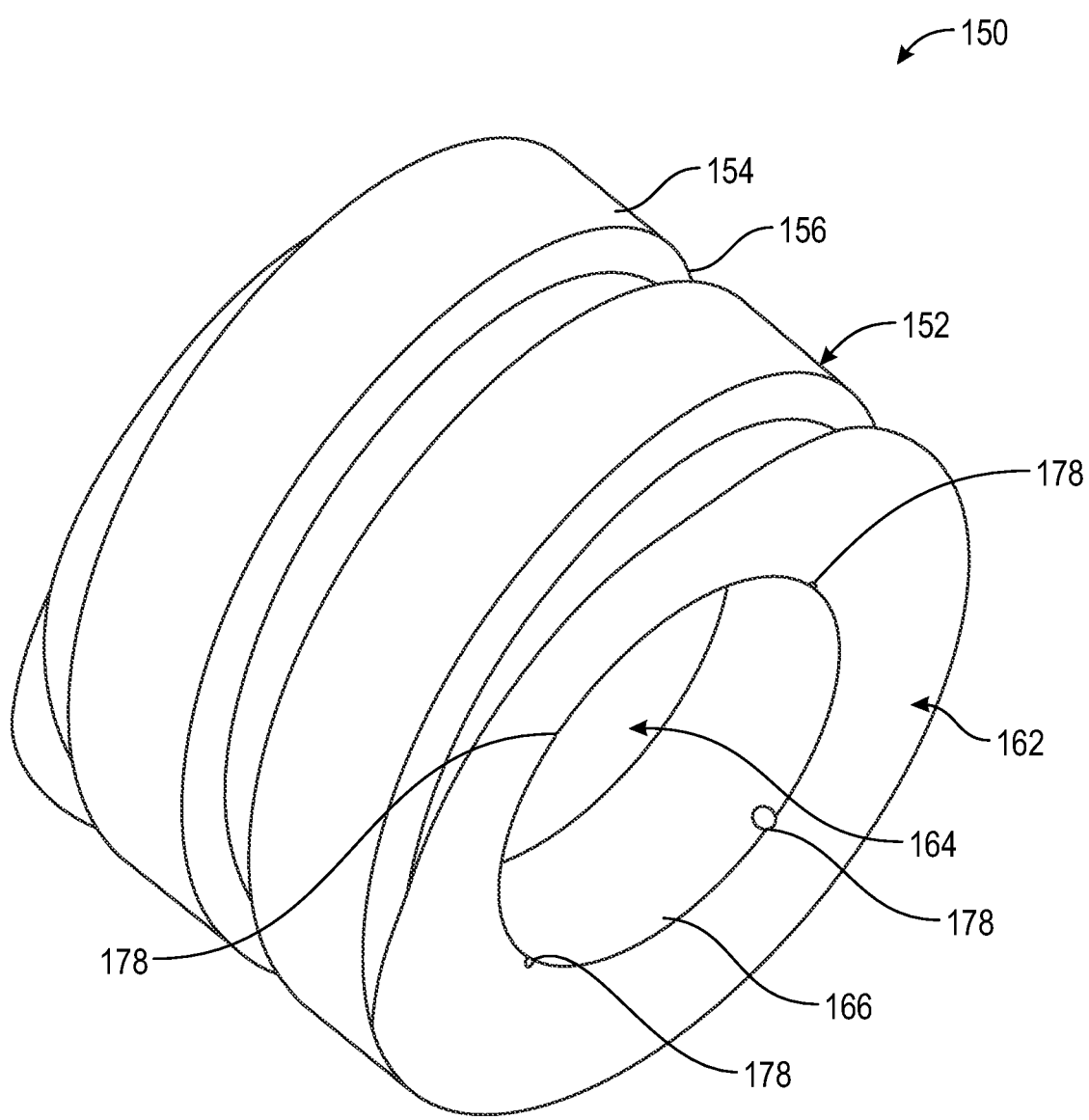
FIG. 4 illustrates a perspective view of a disinfection tip according to an exemplary first embodiment of the disclosure.
Figure 8:
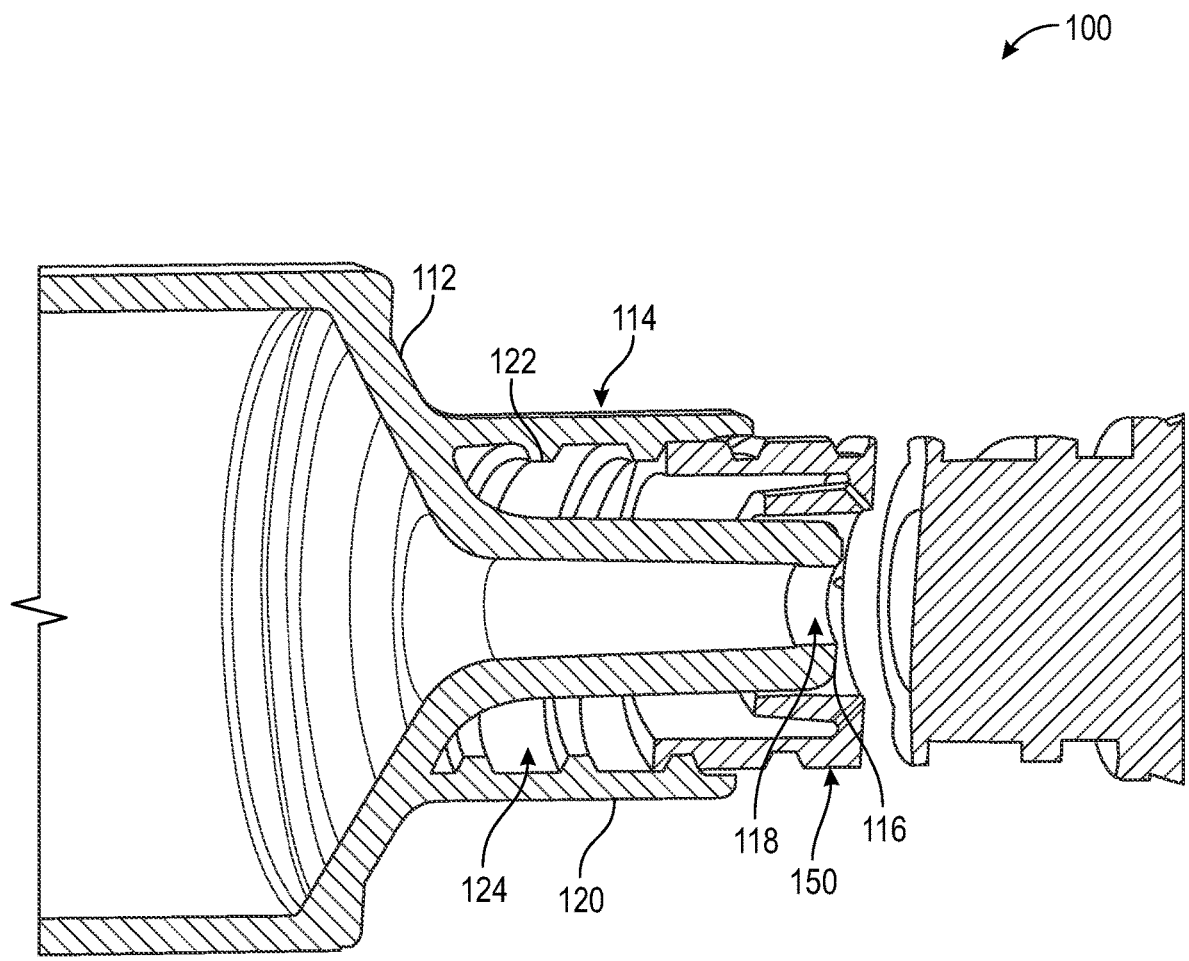
FIG. 8 illustrates yet another cross-sectional view of the disinfection system according to an exemplary first embodiment of the disclosure.
Figure 9:
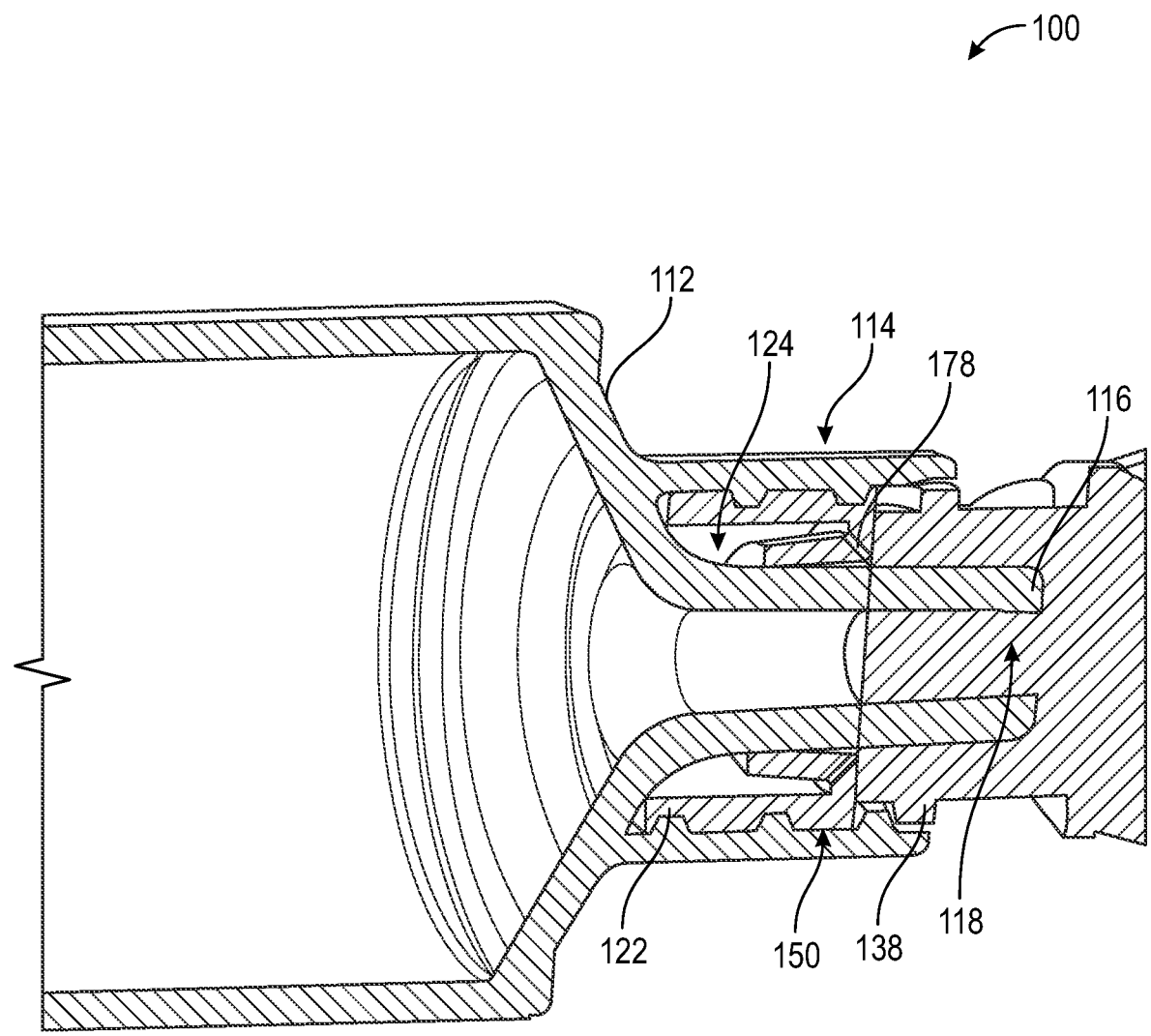
FIG. 9 illustrates yet another cross-sectional view of the disinfection system according to an exemplary first embodiment of the disclosure.

As depicted in FIGS. 3, 8 and 9, in one or more embodiments, the distal portion of the IV connector 130 includes an IV needleless connector, a catheter, a rubber tube and the like. The IV connector 130 includes a cylindrical body 132 having a lumen 134 (not shown) disposed on the proximal end of the cylindrical body. The lumen is covered by a valve 136 which is pierced or opened by the tapered tip 116 of the syringe 110, allowing for fluid communication from the barrel of the syringe 110 through the lumen 118 of the syringe 110 to the lumen 134 of the IV connector 130. In one or more embodiments, the valve 136 is a diaphragm having a slit or a cross-shape slit which remain closed when not pierced or opened by the tapered tip 116 or a needle. An illustration of the IV connector 130 as part of a greater IV line or catheter device is depicted in FIG. 3. It is understood that the illustration of the IV connector 130 is not representative of the distal portion of the IV connector 130.

Figure 5:
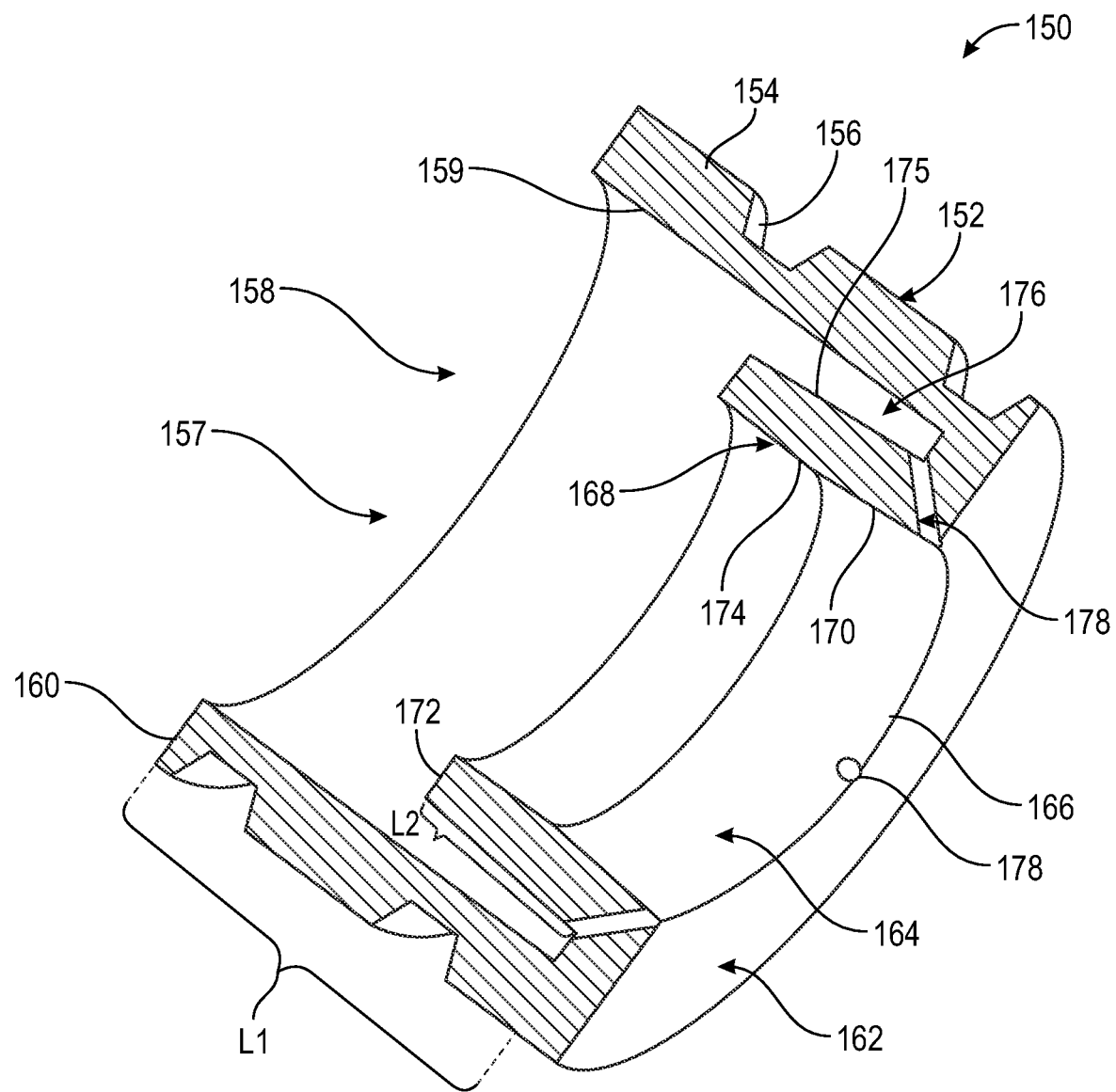
FIG. 5 illustrates a cross-sectional view of the disinfection tip in accordance with an exemplary first embodiment of the disclosure.
Figure 6:
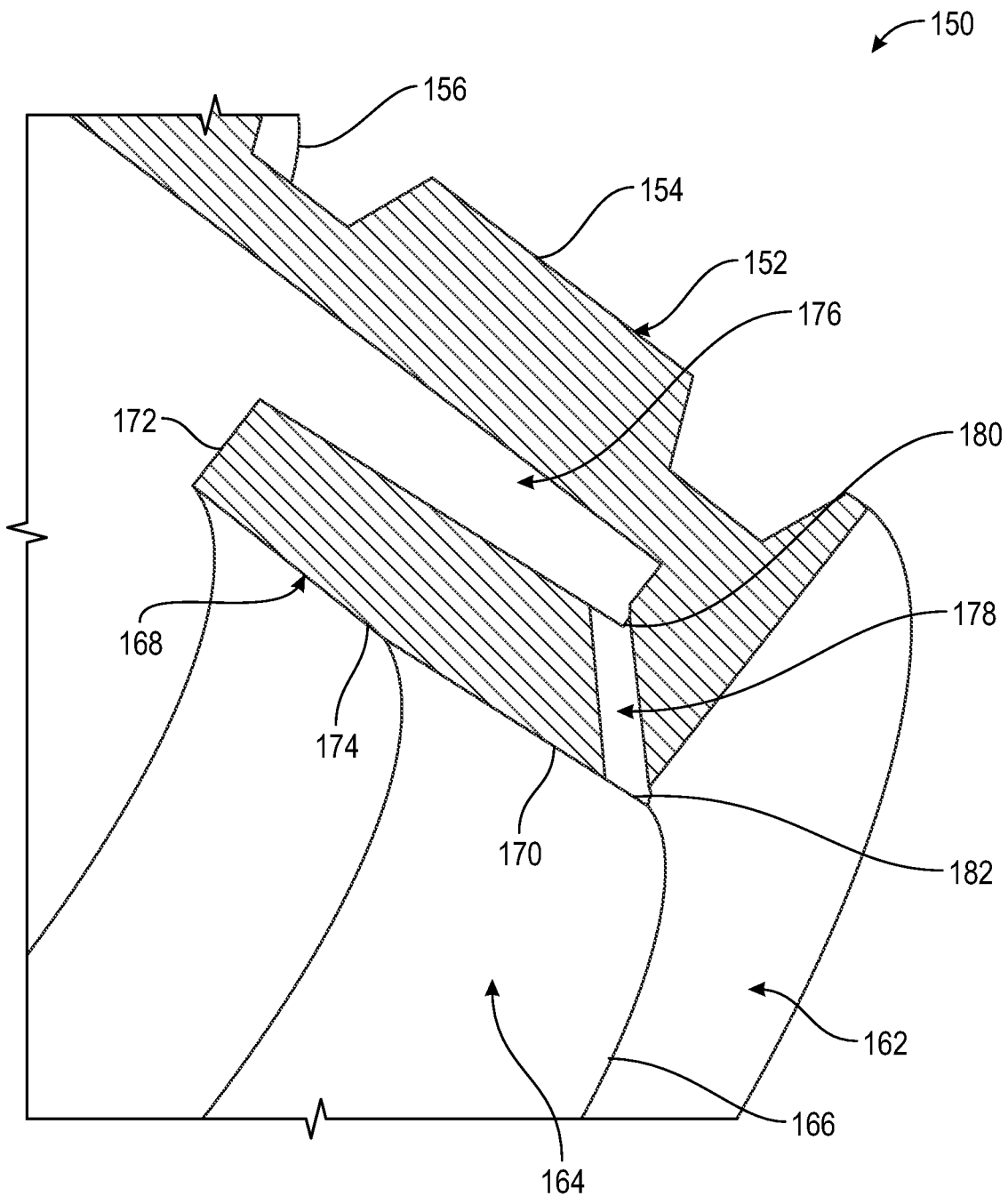
FIG. 6 illustrates a detailed cross-sectional view of the disinfection tip in accordance with an exemplary first embodiment of the disclosure.

As depicted in FIGS. 5 and 6, the disinfection tip 150 comprises a substantially cylindrical outer housing 152 having and outer wall 154, a distal wall 162 and a proximal surface 160. The outer wall 154 includes a plurality of threads 156 for threadedly engaging the plurality of threads 122 of the syringe 110. An aperture 157 extends a length L1 from the proximal surface 160 to the distal wall 162, defining a cavity 158 and an inner wall 159. The distal wall 162 includes a concentrically placed opening 164 defining an inner rim 166, the circumference of opening 164 being smaller than circumference of the cavity 158 defined by the aperture 167. In one or more embodiments, the inner rim 166 is at a right angle relative to the distal wall 162. In one or more embodiments, the inner rim 166 is rounded or chamfered. The diameter/circumference of opening 164 of the inner rim 166 configured to mate with the tapered tip 116 of the syringe 110.

From the inner rim 166 extends an inner housing 168, the inner housing 168 extending in a proximal direction from the inner rim 166 at least partially a length L2 of the outer housing 152. The inner housing 168 is substantially cylindrical in shape, and the inner housing 168 includes an inner proximal surface 172, an inner sidewall 174 and an outer sidewall 175. The outer sidewall 175, the inner wall 159 and the distal wall 162 of the outer housing 152 define a distal chamber 176. In one or more embodiments, the inner proximal surface 172 is conical in shape, conforming to the corresponding conical shape of the tapered tip 116 of the syringe 110. In one or more embodiments, the inner proximal surface 172 is flat and at a right angle with the inner housing 168. In further embodiments, the inner proximal surface 172 is rounded or chamfered as to allow for greater conformity with the conical base 112 of the syringe.

The inner sidewall 174 of the inner housing 168 and the tapered tip 116 of the syringe 110 form a liquid tight seal in which the tapered tip 116 abuts the inner sidewall 174. In one or more embodiments, the liquid tight seal between the inner sidewall 174 of the inner housing 168 and the tapered tip 116 of the syringe 110 is facilitated with an interference fit. The interference fit deforms the inner sidewall 174 of the inner housing 168 in a radial direction as the disinfection tip 150 is further inserted in a proximal direction. In one or more embodiments, the inner sidewall 174 of the inner housing 168 is contoured to not deform as the disinfection tip 150 is further inserted in a proximal direction.

Referring to FIG. 6, at least one jet orifice 178 is radially disposed on the inner rim 166 of the distal wall 162. As shown in FIG. 6, the at least one jet orifice 178 is disposed within the inner housing 168 and transverses the inner sidewall 174 to outer sidewall 175. A jet orifice inlet 180 of the at least one jet orifice 178 is in fluid communication with the distal chamber 176 allowing for fluid to pass from the distal chamber 176 through a jet orifice channel to a jet orifice outlet 182. In the preferred embodiment, the channel is at an acute angle with relation to the distal wall 162 of the outer housing 152, thus directing fluid from the distal chamber 176 in a distal direction towards the center of the outer housing 152. The distal chamber 176, the cavity 158 and the jet orifice 178 are in fluid communication with one another.

Figure 7:
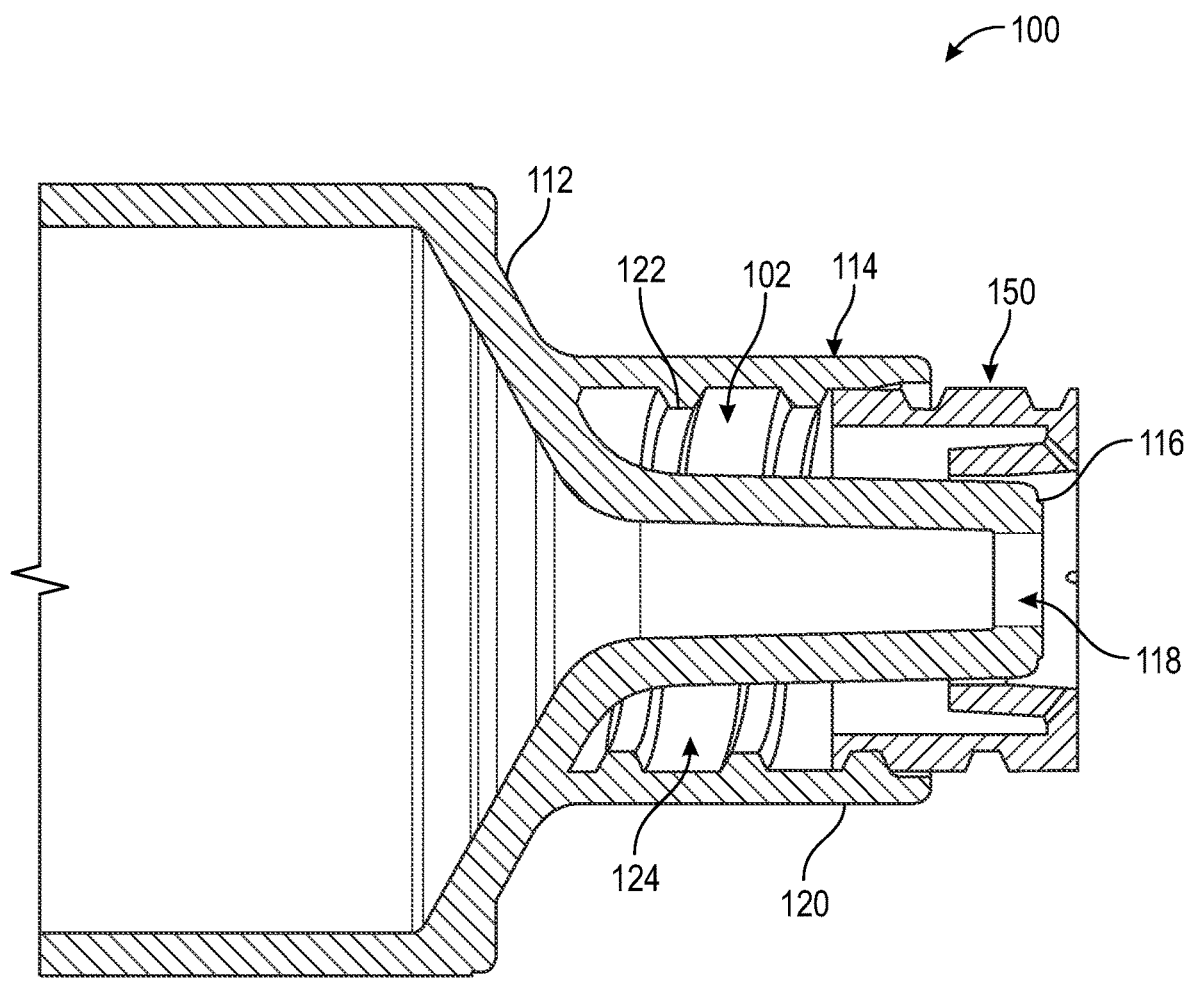
FIG. 7 illustrates a cross-sectional view of the disinfection system according to an exemplary first embodiment of the disclosure.

As shown in FIGS. 7 and 8, the disinfection tip 150 is first disposed at least partially within the luer connector 114 of the syringe 110. In one or more embodiments, the disinfection tip 150 is fully disposed within the luer connector 114. The disinfectant 102 is retained in the disinfectant chamber 124, the disinfection chamber 124 being between the luer connector 114 and the disinfection tip 150. As the IV connector 130 is threaded into the luer connector 114 of the syringe 110 in a proximal direction, the IV connector 130 further guides the disinfection tip 150 into the luer connector 114 in a proximal direction through the transference of axial force in the proximal direction and through the torqueing of the plurality of threads 138 of the IV connector 130 into the plurality of threads 122 of the syringe 110.

In one or more embodiments, the distal wall 162 of the disinfection tip 150 is configured to optimize torque transfer. In one or more embodiments, the distal wall 162 is smooth in order to limit torque coupling during unthreading of the IV connector 130 from the luer connector 114. In one or more embodiments, the distal wall 162 has a rough or textured surface to promote torque coupling. In one or more embodiments, the distal wall 162 has friction enhancing materials or coatings to promote torque coupling. In one or more embodiments, the distal wall 162 has at least one radial spline configured to engage with the IV connector 130. In one or more embodiments, the distal wall 162 has at least one gear tooth configured to engage with a corresponding tooth of the IV connector 130, the at least one gear tooth configured to promote torque coupling. In one or more embodiments, the distal wall 162 includes a plurality of radial peaks, in which an incline of the peak is at a right angle with the distal wall 162 while a decline of the peak is at an acute angle with the distal wall 162, wherein the incline allows for a feature of the IV connector 130 to advance the disinfection tip 150 in the direction of the incline, while the decline prohibits opposite direction of advancement, the direction of advancement being the same direction in which the IV connector 130 is threaded onto the luer connector 114 of the syringe 110.

As the proximal surface 160 of the disinfection tip 150 is advanced further towards the conical base 112 of the syringe 110, the volume of the disinfectant chamber 124 is decreased, causing an increase in pressure of the disinfectant chamber 124. Due to the incompressible nature of liquids, the increase in pressure causes the disinfectant 102 to follow the path of least resistance, traveling through the at least one jet orifice 178, ejecting the liquid in the direction of the at least one jet orifice 178, thereby disinfecting both the luer connector 114 and the IV connector 130. The disinfectant 102 will tend not to ingress into the lumen 118 of the syringe 110 or the lumen of the IV connector 130 due to the interference fit between the tapered tip 116 of the syringe 110 and the lumen of the IV connector 130, as per ISO594-2 standards. Due to the tapered tip 116 extending beyond the outer collar 120 of the syringe 110, the interference fit is engaged before the increase in pressure of the disinfectant chamber 124 causes the disinfectant 102 to eject from the at least one jet orifice 178. As the disinfection tip 150 is advanced even further in the proximal direction, the disinfectant 102, having disinfected the luer connector 114 and the IV connector 130, evacuates from the luer connector 114 through a distal end of the outer collar 120 of the syringe 110 into the atmosphere. Further evacuation of the disinfectant 102 is facilitated by a tolerance gap between the plurality of threads 138 of the IV connector 130 and the plurality of threads 122 of the syringe 110. Disinfectant 102 evacuates through the tolerance gap and into the atmosphere from the distal end of the outer collar 120 of the syringe 110. Such tolerance gap is known in the art and is specified under ISO594-2 standards.

A length of the disinfection tip 150 is defined by the distance from the proximal surface 160 to the distal wall 162. The length is sized to allow for at least one of the plurality of threads 138 of the IV connector 130 to sufficiently engage the plurality of threads 122 of the syringe 110 when the disinfection tip 150 is in a fully threaded position. The fully threaded position is reached when the proximal surface 160 of the disinfection tip 150 abuts or nearly abuts the conical base 112 of the syringe 110. In one or more embodiments, the integrally formed outer collar 120 of the syringe 110, the plurality of threads 122 of the syringe 110 and the tapered tip 116 of the syringe 110 are configured to fully accommodate the disinfection tip 150 while still allowing the standard syringe luer thread depth as required by ISO594-2 standards. Thus, the integrally formed outer collar 120 of the syringe 110, the plurality of threads 122 of the syringe 110 and the tapered tip 116 of the syringe 110 are longer than the features of a common syringe by at least the length of the disinfection tip 150, wherein the disinfection tip 150 may be in the fully threaded position while still permitting the IV connector 130 to sufficiently thread into the luer connector 114 in compliance with ISO594-2 standards.

Thus, instead of disinfecting the luer connector 114 and the IV connector 130 individually, the present disclosure enables a practitioner merely has to thread the IV connector 130 into the luer connector 114. The disinfectant is dispensed or ejected due to the increase in pressure, bathing both the luer connector 114 and the IV connector 130.

Furthermore, because the length of the disinfection tip 150 allows for the disinfection tip 150 to remain fully threaded into the luer connector 114 of the syringe 110 during engagement of the IV connector 130 and further administration of the medical procedure, the practitioner does not have to take any additional steps in disinfecting the connection. Thus, instead of individually disinfecting the luer connector 114 and the IV connector 130 individually, or even removing the means of disinfection, the practitioner merely has to thread the IV connector 130 into the luer connector 114 of the syringe and the disinfection system 100 can be normally used.

In further embodiments, the surface of the distal wall 162 of the disinfection tip 150 also defines an engagement surface where a peelable seal is secured. In one or more embodiments, the disinfection tip 150 can include the peelable seal covering the opening 164 of the disinfection tip 150 and the at least one jet orifice 178 to seal the disinfectant 102 within the disinfectant chamber 124 of the syringe 110 and the disinfection tip 150 prior to use of the syringe 110 and the disinfection tip 150. The peelable seal minimizes entry of potential particulate hazard and also provides a substantially impermeable enclosure for the disinfection tip 150, provides a leak prevention and protection enclosure, protects the contents of the disinfectant chamber 124 of the syringe 110 and the disinfection tip 150 prior to use of the syringe 110 and the disinfection tip 150 and/or maintains a sealed, sterilized environment. The peelable seal provides a sufficient seal at a range of temperatures, pressures, and humidity levels.

The disinfection tip 150 is designed to be compatible in interacting with the disinfectant 102. In one or more embodiments, the disinfectant 102 includes variations of alcohol or chlorhexidine. In one or more embodiments, the disinfectant 102 includes variations of alcohol or chlorhexidine. In one or more embodiments, the disinfectant 102 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant 102 comprises at least one of chlorhexidine gluconate and chlorhexidine diacetate. In one or more embodiments, the disinfectant 102 is a fluid or a gel.

In one or more embodiments the disinfection tip 150 can be deformable and is of polypropylene, polyethylene or TPE material. In further embodiments, the syringe 110, disinfection tip 150 and/or IV connector 130 are made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the syringe 110, disinfection tip 150 and/or IV connector 130 comprises a polypropylene or polyethylene material.

In one or more embodiments, the IV connector 130 may be selected from the group consisting essentially of needle-free connectors, catheter luer connectors, stopcocks, and hemodialysis connectors on primary IV gravity sets, secondary IV gravity sets, extension sets, and infusion or syringe pump sets. In one or more embodiments, the male connector may be selected from the group consisting essentially of needle-free connectors, catheter luer connectors, stopcocks, and hemodialysis connectors.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments,"

"in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection tip comprising:
    a substantially cylindrical outer housing, the outer housing having an outer wall, a distal wall, and an open proximal surface;
    a cavity defined by an aperture extending from the open proximal surface to the distal wall, the distal wall having an opening defining an inner rim and an inner wall;
    a substantially cylindrical inner housing extending from the inner rim in a proximal direction at least partially a length of the outer housing, the inner housing having an inner proximal surface, an inner sidewall and an outer sidewall, the inner sidewall abuts a tapered tip of a luer connector creating a liquid tight seal when the disinfection tip is disposed at least partially within the luer connector;
    a distal chamber defined by the outer sidewall of the inner housing, the inner wall and the distal wall of the outer housing, the distal chamber being in fluid communication with the cavity, the distal chamber retaining a disinfectant or antimicrobial agent when the disinfection tip is at least partially disposed within an outer wall of the luer connector of the luer connector; and
    at least one jet orifice radially disposed on the inner rim, the jet orifice having an inlet, an outlet and a channel extending from the inlet to the outlet.

2. The disinfection tip of claim 1, wherein the outer distal wall of the outer housing of the disinfection tip is capable of being advanced against an IV connector, whereby a tapered tip of the luer connector adapted to engage with a lumen of the cylindrical body of the IV connector, an advancement causing the disinfectant to be ejected from the at least one orifice.

3. The disinfection tip of claim 2, wherein the disinfectant disinfects the lumen of the IV connector upon advancement of the disinfection tip.

4. The disinfection tip of claim 2, wherein the disinfectant disinfects the cylindrical body of the IV connector upon advancement of the disinfection tip.

5. The disinfection tip of claim 2, wherein the IV connector is capable of sufficiently threading into the luer connector when the proximal surface of the disinfection tip abuts a conical base of the syringe.

6. The disinfection tip of claim 2, wherein the IV connector is capable of sufficiently threading into the luer connector when the proximal surface of the disinfection tip abuts a conical base of the syringe in compliance with ISO594-2 standards.

7. The disinfection tip of claim 1, further comprising a plurality of threads on the outer wall of the disinfection tip for threadedly engaging a plurality of threads of a syringe.

8. The disinfection tip of claim 7, wherein threading the IV connector onto the luer connector transfers an axial force and torque to the disinfection tip, the threading of the IV connector causing an advancement of the disinfection tip.

9. The disinfection tip of claim 8, wherein the distal wall of the disinfection tip is smooth in order to limit torque coupling during unthreading of the IV connector from the luer connector.

10. The disinfection tip of claim 8, wherein the distal wall of the disinfection has a rough or textured surface to promote torque coupling.

11. The disinfection tip of claim 8, wherein the distal wall of the disinfection has friction enhancing materials or coatings to promote torque coupling.

12. The disinfection tip of claim 8, wherein the distal wall of the disinfection has at least one radial spline configured to engage with the IV connector.

13. The disinfection tip of claim 8, wherein the distal wall of the disinfection has at least one gear tooth configured to engage with a corresponding tooth of the IV connector, the at least one gear tooth configured to promote torque coupling.

14. The disinfection tip of claim 8, wherein the distal wall of the disinfection tip includes a plurality of radial peaks, in which an incline of the peak is at a right angle with the distal wall while a decline of the peak is at an acute angle with the distal wall, wherein the incline allows for a feature of the IV connector to advance the disinfection tip in the direction of the incline, while the decline prohibits opposite direction of advancement, the direction of advancement being the same direction in which the IV connector is threaded onto the luer connector of the luer connector.

15. The disinfection tip of claim 8, wherein the advancement of the disinfection tip allows for evacuation of the disinfectant though a tolerance gap between a plurality of threads of the IV connector and a plurality of threads of a syringe.

16. The disinfection tip of claim 7, wherein at least one thread of the IV connector fully engages the plurality of threads of the disinfection tip.

17. The disinfection tip of claim 1, wherein the inlet of the at least one jet orifice is in fluid communication with the distal chamber allowing for the disinfectant or antimicrobial agent to pass from the distal chamber through the channel to the outlet.

18. The disinfection tip of claim 1, wherein the outlet of the at least one jet orifice is disposed on the rim.

19. The disinfection tip of claim 1, wherein the outlet of the at least one jet orifice is positioned to direct the disinfectant or antimicrobial agent from the distal chamber in a distal direction towards a center of the outer housing.

20. The disinfection tip of claim 1, wherein insertion of the disinfection tip allows a volume of the distal chamber to reduce and expel disinfectant or antimicrobial agent through the at least one jet orifice.

* * * * *